United States Patent
Yoshikawa et al.

(10) Patent No.: US 7,602,961 B2
(45) Date of Patent: Oct. 13, 2009

(54) REFERENCE DATA GENERATING METHOD, PATTERN DEFECT CHECKING APPARATUS, PATTERN DEFECT CHECKING METHOD, REFERENCE DATA GENERATING PROGRAM, AND SEMICONDUCTOR DEVICE MANUFACTURING METHOD

(75) Inventors: Ryoji Yoshikawa, Yokohama (JP); Hidehiro Watanabe, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 756 days.

(21) Appl. No.: 11/024,198

(22) Filed: Dec. 29, 2004

(65) Prior Publication Data
US 2005/0169513 A1 Aug. 4, 2005

(30) Foreign Application Priority Data
Jan. 5, 2004 (JP) ............................. 2004-000516

(51) Int. Cl.
*G06K 9/00* (2006.01)
(52) U.S. Cl. ...................................... 382/148; 382/144
(58) Field of Classification Search .................. 382/144, 382/148
See application file for complete search history.

(56) References Cited

U.S. PATENT DOCUMENTS

| 4,628,531 | A | * | 12/1986 | Okamoto et al. | ............. | 382/144 |
| 5,475,766 | A | * | 12/1995 | Tsuchiya et al. | ............. | 382/144 |
| 5,574,800 | A | * | 11/1996 | Inoue et al. | .................. | 382/149 |
| 5,807,649 | A | * | 9/1998 | Liebmann et al. | ............... | 430/5 |
| 6,083,275 | A | * | 7/2000 | Heng et al. | ..................... | 716/19 |
| 6,504,947 | B1 | * | 1/2003 | Nozaki et al. | ................ | 382/148 |
| 6,721,938 | B2 | * | 4/2004 | Pierrat et al. | .................. | 716/19 |

(Continued)

FOREIGN PATENT DOCUMENTS

JP  2000-199709  7/2000

(Continued)

OTHER PUBLICATIONS

Yoshikawa, R. et al., "257nm Wavelength Mask Inspection for 62nm Node Reticles", Digest of Papers Photomask Japan 2004, pp. 73-74, (2004).

(Continued)

*Primary Examiner*—Samir A. Ahmed
*Assistant Examiner*—Li Liu
(74) *Attorney, Agent, or Firm*—Finnegan, Henderson, Farabow, Garrett & Dunner, L.L.P.

(57) ABSTRACT

A method of generating reference data is disclosed, in which two-value or multi-value gradated data of pixels is obtained in units of pixels from a design data of a pattern to be formed on an object, a processed data is obtained by carrying out calculations to the gradated data, and a reference data for use in a comparison with a sensed data obtained by image-picking up a pattern formed on the object is obtained based on the processed data, the method comprising carrying out a first calculation including a predetermined parameter to a value of an gradated data of a targeted pixel among the pixels to obtain a first processed data, and carrying out a second calculation including a predetermined parameter to the values of the gradated data of the targeted pixel and pixels located at the periphery of the targeted pixel to obtain a second processed data.

12 Claims, 17 Drawing Sheets

U.S. PATENT DOCUMENTS

2002/0051566 A1* 5/2002 Yamashita .................. 382/151

FOREIGN PATENT DOCUMENTS

JP 2001-272217 10/2001

JP 2002-107309 4/2002

OTHER PUBLICATIONS

Notification of Reasons for Rejection from the Japanese Patent Office, mailed Oct. 31, 2006, in Japanese Patent Application No. 2004-000516, and English translation thereof.

* cited by examiner

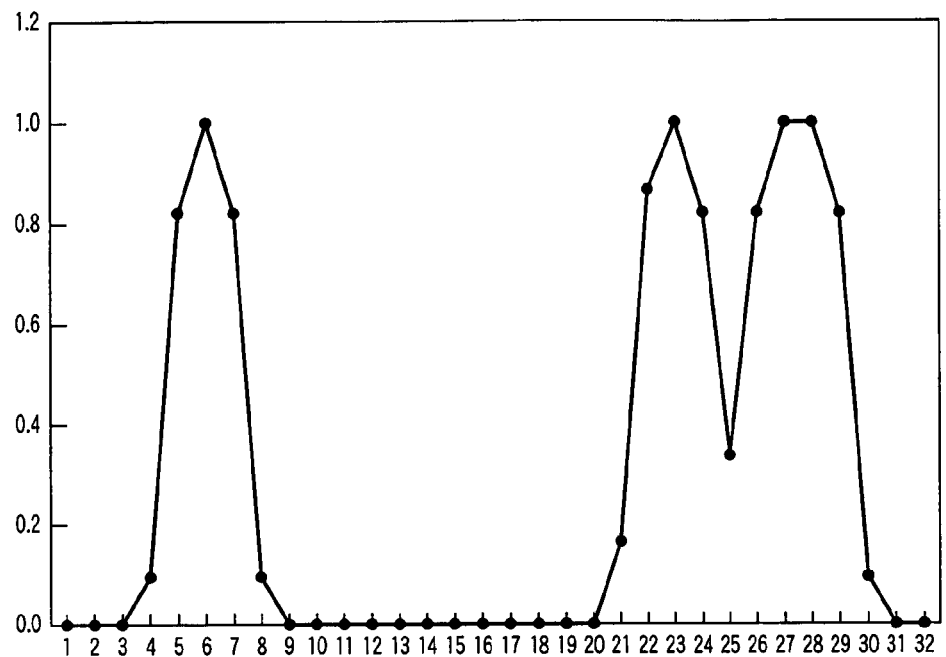
F I G. 12
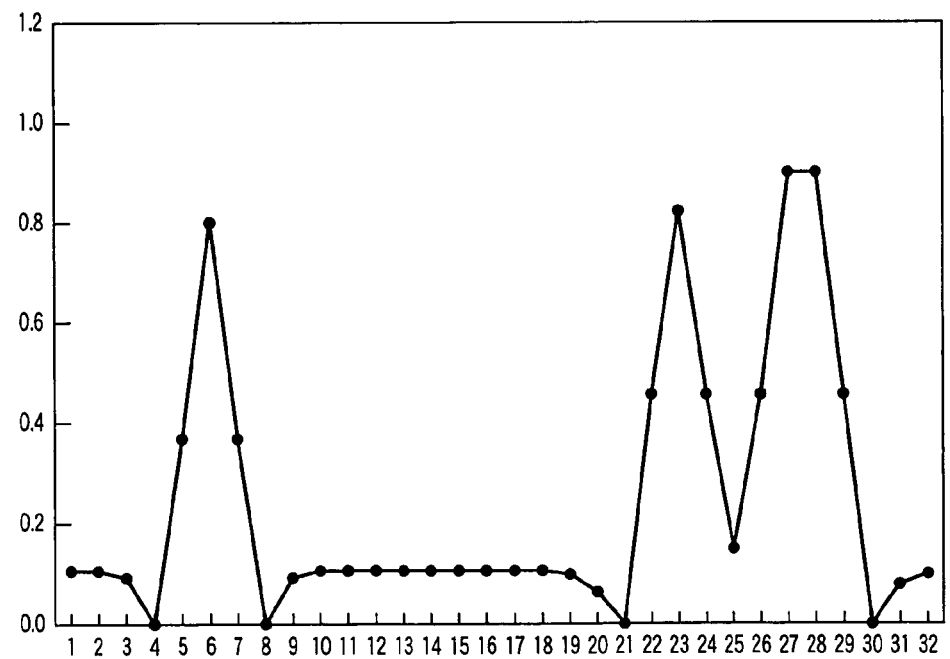
F I G. 14

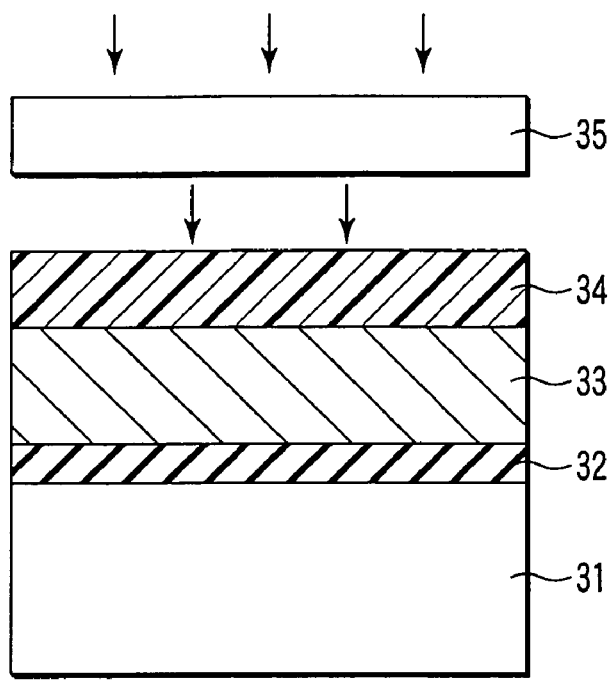
F I G. 19
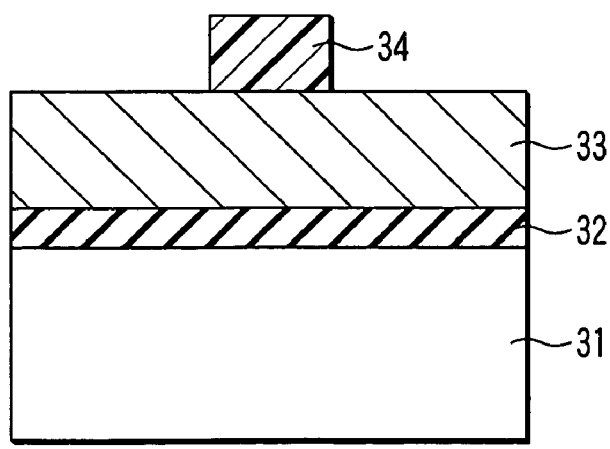
F I G. 20

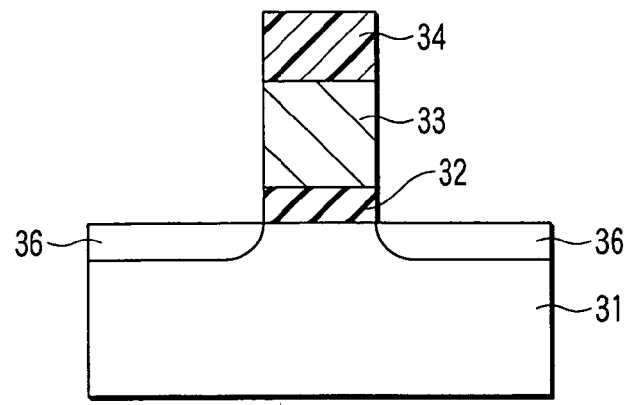
F I G. 21
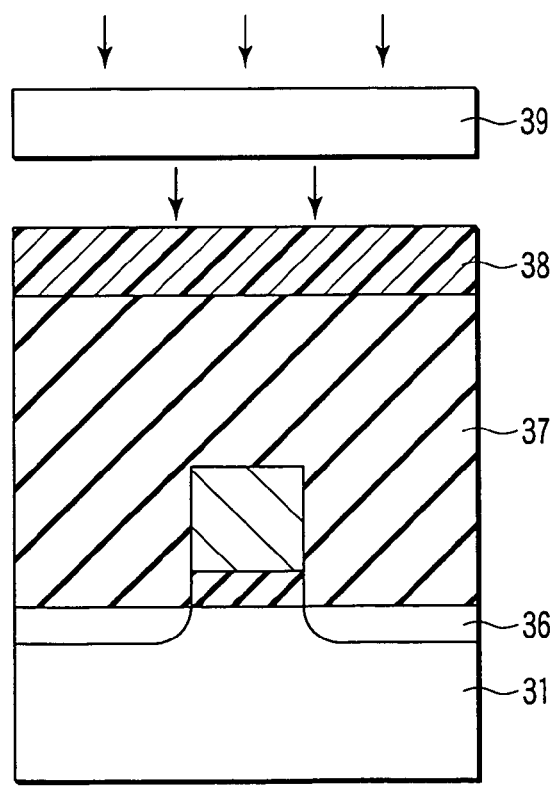
F I G. 22

REFERENCE DATA GENERATING METHOD, PATTERN DEFECT CHECKING APPARATUS, PATTERN DEFECT CHECKING METHOD, REFERENCE DATA GENERATING PROGRAM, AND SEMICONDUCTOR DEVICE MANUFACTURING METHOD

CROSS-REFERENCE TO RELATED APPLICATIONS

This application is based upon and claims the benefit of priority from prior Japanese Patent Application No. 2004-000516, filed Jan. 5, 2004, the entire contents of which are incorporated herein by reference.

BACKGROUND OF THE INVENTION

1. Field of the Invention

The present invention relates to a reference data generating method for use in making a comparison with sensed data obtained by image-picking up a pattern formed on a photo mask, a semiconductor wafer or the like.

In addition, the present invention relates to a pattern defect checking apparatus and checking method for checking a pattern defect by comparing a sensed data obtained by image-picking up a pattern formed on a photo mask, a semiconductor wafer or the like with a reference data obtained by expanding a design data of the pattern.

Further, the present invention relates to a reference data generating program of generating a reference data for use in pattern defect check by a computer.

Also, the present invention relates to a method of manufacturing a semiconductor device by using a photo mask after checking a pattern defect by comparing a sensed data obtained by image-picking up a pattern formed on a photo mask with a reference data obtained by expanding a design data of the pattern.

2. Description of the Related Art

Conventionally, in the case of carrying out a defect check of a pattern formed on a photo mask for use in manufacturing semiconductor devices, light beams are radiated onto a photo mask from a light beam source such as a mercury lamp or a laser oscillation source. A pattern image data (sensed data) obtained by image-picking up light beams passed through the mask is compared with a reference data obtained by expanding a design data of the pattern, to detect an unmatched portion as a defect. In recent years, a photo mask pattern has been finer, and the size of a defect to be detected has been smaller than 100 nm. In addition, it is necessary to carry out a defect check with high sensitivity for a mask using a high resolution technique such as a phase shift or optical proximity effect correction.

In order to enhance detection sensitivity, it is necessary to enhance alignment between a reference data obtained by expanding a design data of a pattern to be formed on an object and a sensed data obtained by image-picking up a pattern formed on the object. In a conventional reference data generating method, a feature of a pattern targeted to be checked is geometrically calculated, and the calculated pattern feature is optically calculated (for example, Jpn. Pat. Appln. KOKAI Publication No. 2002-107309).

In such a conventional method, however, the calculation result largely depends on a calculation model, and figures smaller than an inspection pixel size may be arbitrarily calculated, and thus the alignment between the reference data and the sensed data is low. In particularly, in the optical proximity effect correction mask, dimensions of an assisting pattern are extremely small to a line width of a main pattern, thus making it difficult to obtain a reference data with high accuracy. In addition, a large amount of time has been required for calculation because geometrical and optical calculations are carried out.

As described above, in a pattern defect check for checking a pattern formed on an object targeted to be checked, it is necessary to provide a reference data from a pattern design data. However, a large amount of time is required to provide a reference data, and it is difficult to provide a reference data with high alignment with a sensed data.

BRIEF SUMMARY OF THE INVENTION

According to an aspect of the present invention, there is provided a method of generating reference data, in which two-value or multi-value gradated data of pixels arranged in a two-dimensional form is obtained in units of pixels from a design data of a pattern to be formed on an object, a processed data is obtained by carrying out calculations to the gradated data, and a reference data for use in a comparison with a sensed data obtained by image-picking up a pattern formed on the object is obtained based on the processed data, the method comprising:

carrying out a first calculation including a predetermined parameter to a value of an gradated data of a targeted pixel among the pixels to obtain a first processed data; and carrying out a second calculation including a predetermined parameter to the values of the gradated data of the targeted pixel and pixels located at the periphery of the targeted pixel to obtain a second processed data.

According to another aspect of the present invention, there is provided a pattern defect detecting apparatus in which a sensed data is obtained by image-picking up a pattern formed on an object, two-value or multi-value gradated data of pixels arranged in a two-dimensional form is obtained in units of pixels from a design data of a pattern to be formed on the object, a processed data is obtained by carrying out calculations to the gradated data, and a reference data is obtained based on the processed data, and the reference data is compared with the sensed data, the apparatus comprising:

a first calculating circuit configured to carry out a calculation including a predetermined parameter to a value of an gradated data of a targeted pixel among the pixels to obtain a first processed data; and a second calculating circuit configured to carry out a calculation including a predetermined parameter to the values of the gradated data of the targeted pixel and pixels located at the periphery of the targeted pixel to obtain a second processed data.

According to a further aspect of the present invention, there is provided a reference data generating program readable and executable by a computer, in which two-value or multi-value gradated data of pixels arranged in a two-dimensional form is obtained in units of pixels from a design data of a pattern to be formed on an object, a processed data is obtained by carrying out calculations to the gradated data, and a reference data for use in a comparison with a sensed data obtained by image-picking up a pattern formed on the object is obtained based on the processed data, the program comprising:

a first calculation to carry out a calculation including a predetermined parameter to a value of an gradated data of a targeted pixel among the pixels to obtain a first processed data; and a second calculation to carry out a calculation including a predetermined parameter to the values of the gradated data of the targeted pixel and pixels located at the periphery of the targeted pixel to obtain a second processed data.

According to a further aspect of the present invention, there is provided a pattern defect detecting apparatus in which a sensed data obtained by image-picking up a pattern formed on an object is compared with a reference data obtained by developing a design data of a pattern to be formed on the object to detect a defect of the pattern formed on the object, comprising:

a gradated data generating circuit configured to generate two-value or multi-value gradated data of pixels in units of pixels from the design data;

a reference data generating circuit configured to generate a first processed data by multiplying a gradated value of a targeted pixel in the gradated data by a first coefficient in accordance with gradated values of pixels located at the periphery of the targeted pixel, a second processed data by rounding up a gradated value of the pixel in the first processed data by a first threshold value, a third processed data by rounding down a gradated value of the pixel in the second processed data by a second threshold value, a fourth processed data by multiplying a gradated value of the pixel in the third processed data by a second coefficient, and the reference data based on the fourth processed data; and a pattern defect detecting circuit configured to compare the reference data with the sensed data.

According to a further aspect of the present invention, there is provided a method of detecting a pattern defect, in which a sensed data obtained by image-picking up a pattern formed on an object is compared with a reference data obtained by developing a design data of a pattern to be formed on the object to detect a defect of the pattern formed on the object, comprising:

generating two-value or multi-value gradated data of pixels in units of pixels from the design data, and generating a first processed data by multiplying a gradated value of a targeted pixel in the gradated data by a first coefficient in accordance with gradated values of pixels located at the periphery of the targeted pixel;

generating a second processed data by rounding up a gradated value of the pixel in the first processed data by a first threshold value;

generating a third processed data by rounding down a gradated value of the pixel in the second processed data by a second threshold value;

generating a fourth processed data by multiplying a gradated value of the pixel in the third processed data by a second coefficient; and comparing the reference data obtained based on the fourth processed data with the sensed data.

According to a further aspect of the present invention, there is provided a reference data generating program readable and executable by a computer, in which a reference data for use in a comparison with a sensed data obtained by image-picking up a pattern is obtained by developing a design data of the pattern under control of a computer, comprising: generating two-value or multi-value gradated data of pixels in units of pixels from the design data; generating a first processed data by multiplying a gradated value of a targeted pixel in the gradated data by a first coefficient in accordance with a gradated value of a pixel located at the periphery of the targeted pixel; generating a second processed data by rounding up a gradated value of the pixel in the first processed data by a first threshold value; generating a third processed data by rounding down a gradated value of the pixel in the second processed data by a second threshold value; and generating a fourth processed data by multiplying a gradated value of the pixel in the third processed data by a second coefficient.

According to a further aspect of the present invention, there is provided a method of manufacturing a semiconductor device comprising:

detecting a pattern defect of a photo mask having a semiconductor circuit pattern, by using the method of detecting a pattern defect, according to some embodiments as disclosed herein;

transferring the semiconductor circuit pattern on a semiconductor substrate, by using the photo mask after detecting the pattern defect; and forming a semiconductor circuit having the semiconductor circuit pattern on the semiconductor substrate.

BRIEF DESCRIPTION OF THE SEVERAL VIEWS OF THE DRAWING

FIG. 12 is a graph showing a profile of the processing data shown in FIG. 11, taken along the line 12-12 shown in FIG. 11.

FIG. 14 is a graph showing a profile of the processing data shown in FIG. 13, taken along the line 14-14 shown in FIG. 13.

FIG. 19 is a cross sectional view showing a device structure in a step of a method of manufacturing a semiconductor device according to another embodiment of the present invention, which is used to explain the manufacturing method.

FIG. 20 is a cross sectional view showing a device structure in a step following to the step in FIG. 19 of the method of manufacturing the semiconductor device according to the embodiment of the present invention, which is used to explain the manufacturing method of the semiconductor device.

FIG. 21 is a cross sectional view showing a device structure in a step following to the step in FIG. 20 of the method of manufacturing the semiconductor device according to the embodiment of the present invention, which is used to explain the manufacturing method of the semiconductor device.

FIG. 22 is a cross sectional view showing a device structure in a step following to the step in FIG. 21 of the method of manufacturing the semiconductor device according to the embodiment of the present invention, which is used to explain the manufacturing method of the semiconductor device.

DETAILED DESCRIPTION OF THE INVENTION

Hereinafter, embodiments of the present invention will be described with reference to the accompanying drawings.

Figure 1:
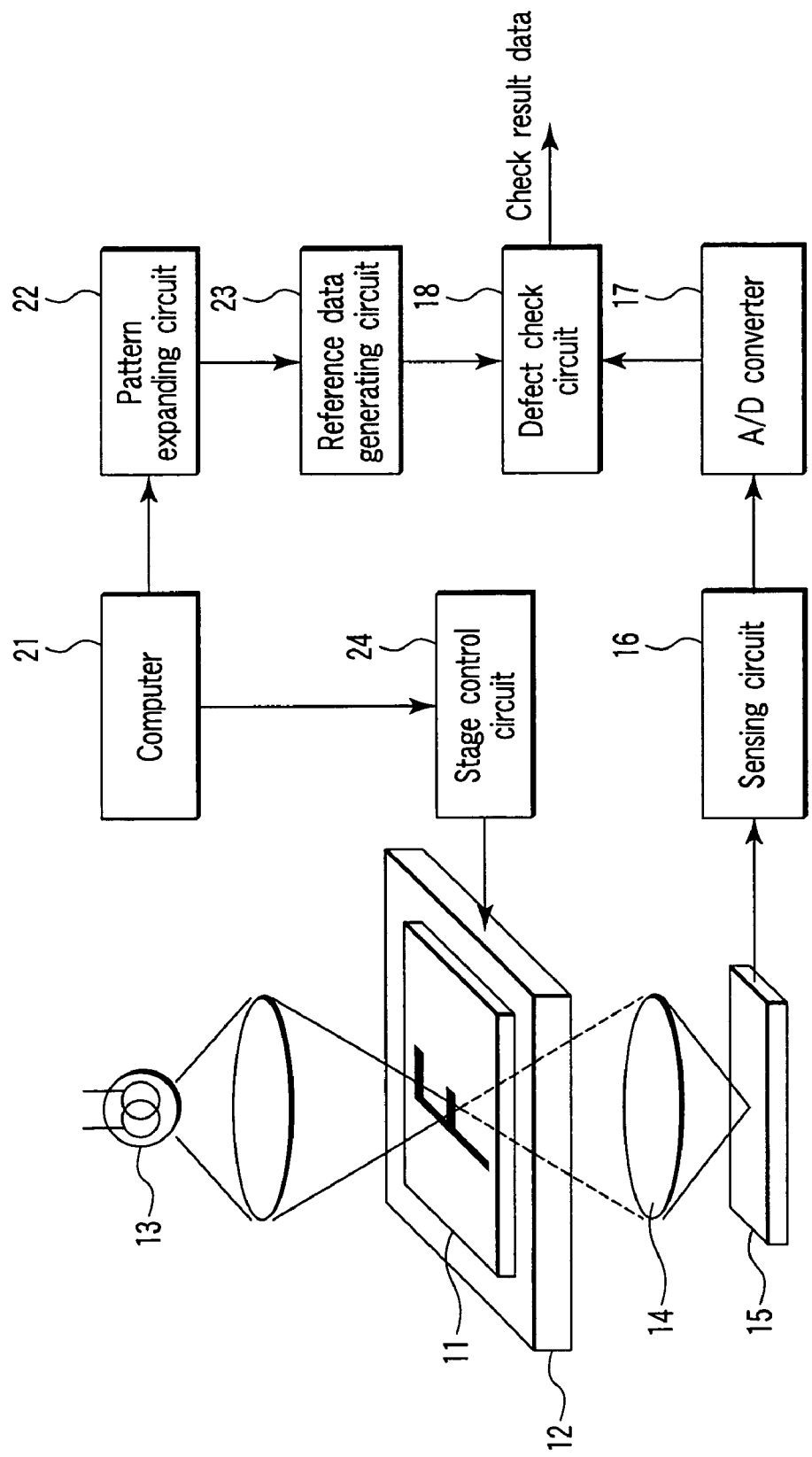
FIG. 1 is a schematic diagram showing a construction of a pattern defect checking apparatus according to an embodiment of the present invention.

FIG. 1 is a schematic diagram showing a structure of a pattern defect checking apparatus according to an embodiment of the present invention.

In FIG. 1, a photo mask 11 has a pattern of an LSI or the like formed thereon and is placed on an XY stage 12. Light beams are radiated onto the photo mask 11 from a light source 13. Those of the light beams, that are passed through the photo mask 11, are focused on an image pickup device 15 via an objective lens 14 to form an optical image of the pattern. The optical image is measured by a sensing circuit 16, and then converted into a digital signal by an A/D (Analog-to-Digital) converter 17. The digital signal is transmitted to a defect check circuit 18. The optical image may be obtained by using reflected light beams from the mask, or mixture light beams of the passed light beams and the reflected light beams, depending on characteristics of the mask.

On the other hand, a design data of the pattern is transmitted to a pattern expanding circuit 22 from a computer 21, and the transmitted data is expanded into two-value or multi-value gradated data of pixels arranged in two-dimensional form in units of pixel by the pattern expanding circuit 22. The gradated data (expanded pattern data) is transmitted to a reference data generating circuit 23, and a reference data is obtained by the reference data generating circuit 23. The reference data contains a change of a shape of the pattern caused by an etching process or the like carried out when the pattern is formed on the photo mask 11. The reference data is transmitted to a defect check circuit 18.

The sensed data obtained by sensing circuit 16 and transmitted to the defect check circuit 18 via the A/D converter 17 (i.e., a photo mask pattern image) is compared with reference data transmitted from the reference data generating circuit 23 by the defect check circuit 18 to check a defect of the pattern formed on the photo mask 11. The XY stage 12 is movable in an XY direction by a stage control circuit 24, which is operated by a command from the computer 21.

Now, a description will be given with respect to a pattern defect checking method in accordance with the present embodiment, in particular, a reference data generating method, with reference to FIGS. 2 to 18.

Figure 2:
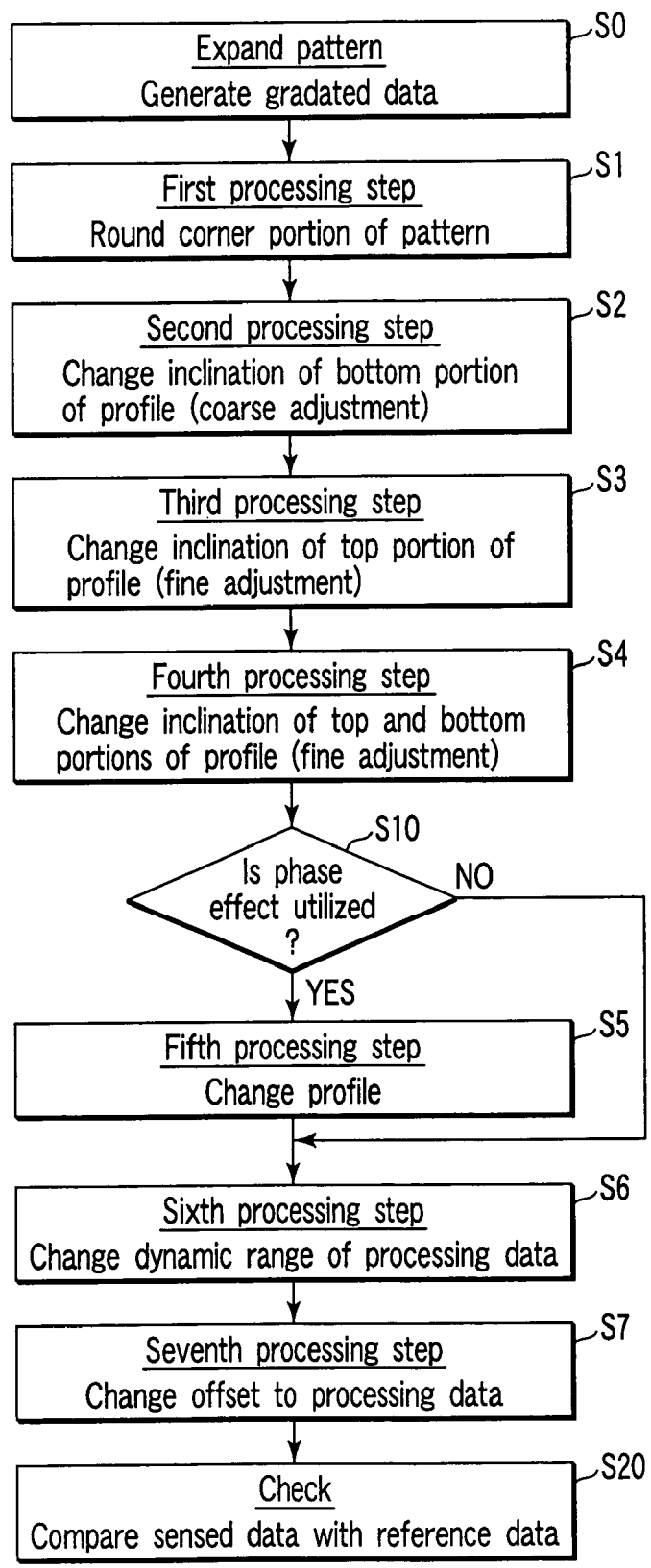
FIG. 2 is a flow chart adopted to illustrate a pattern defect checking method in the present embodiment.

FIG. 2 is a flow chart showing a pattern defect checking method in accordance with the present embodiment.

Figure 3:
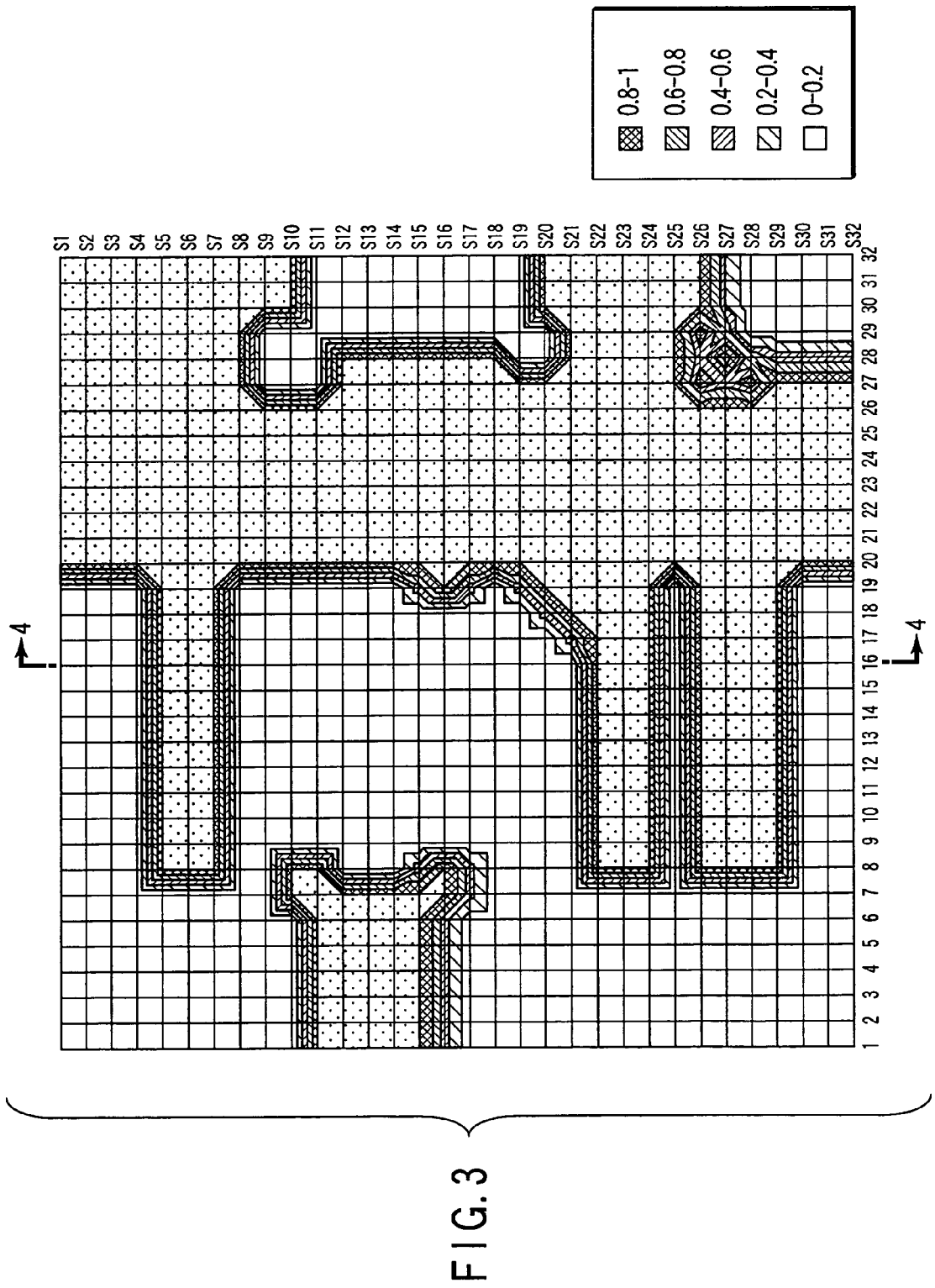
FIG. 3 is a graph showing gradated data (graphic data) obtained from pattern design data.
Figure 4:
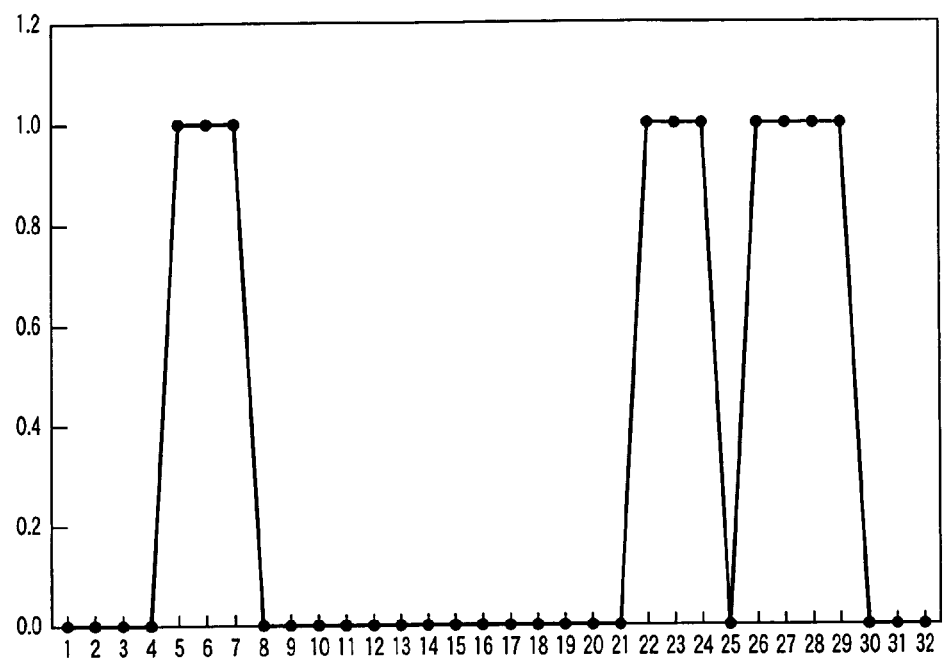
FIG. 4 is a graph showing a profile of the graphic data, taken along the line 4-4 shown in FIG. 3.

FIG. 3 is a graph showing a gradated data obtained by expanding a design data of a pattern, and FIG. 4 is a graph showing a profile of the gradated data shown in FIG. 3, taken along the lines 4-4 shown in FIG. 3.

As shown in FIG. 3, the gradated data is a graphic data, and composed of rectangular portions.

First, as shown in FIG. 3, two-value or multi-value of pixels arranged in a two-dimensional form gradated data in units of pixel is obtained by expanding a design data of a pattern to be formed by the pattern expanding circuit 22 (step S0). The gradated data is transmitted to the reference data generating circuit 23.

The reference data generating circuit 23 carries out the following calculations sequentially. These calculations may be carried out by hardware of the reference data generator circuit 23 or may be carried out in accordance with a program by the computer 21.

First, the following calculation (first processing step: step S1) is carried out for the figures of the gradated data (graphic data) shown in FIG. 3.

$$a(i,j)=[a(i,j)+\{a(i-1,j)+a(i+1,j)+a(i,j-1)+a(i,j+1)\}/4+ \{a(i-1,j-1)+a(i+1,j+1)+a(i+1,j-1)+a(i-1,j+1)\}/8]/2.5 \quad (1)$$

Figure 6:
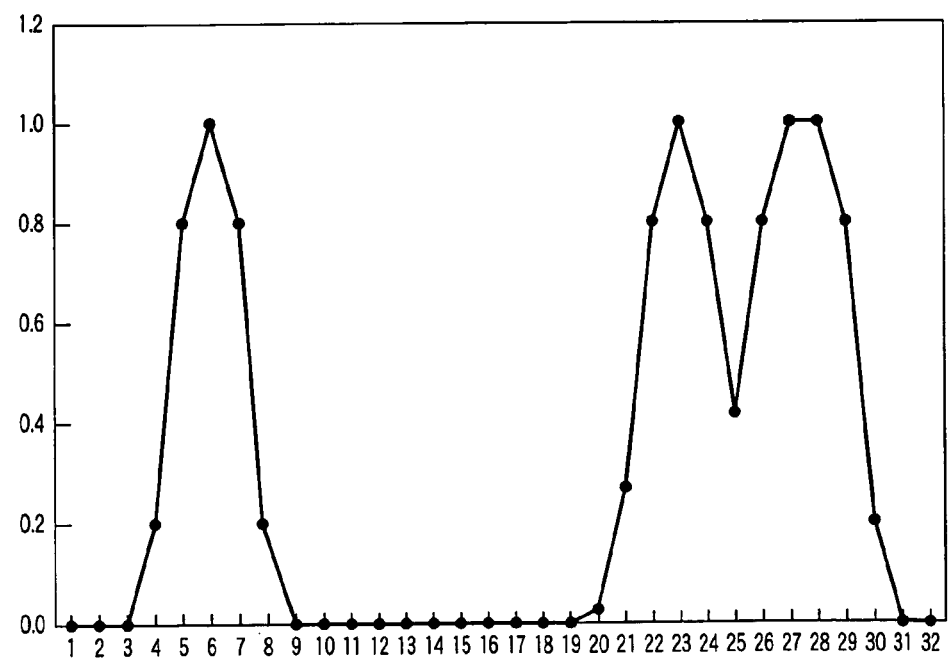
FIG. 6 is a graph showing a profile of the processing data shown in FIG. 5, taken along the line 6-6 shown in FIG. 5.
Figure 5:
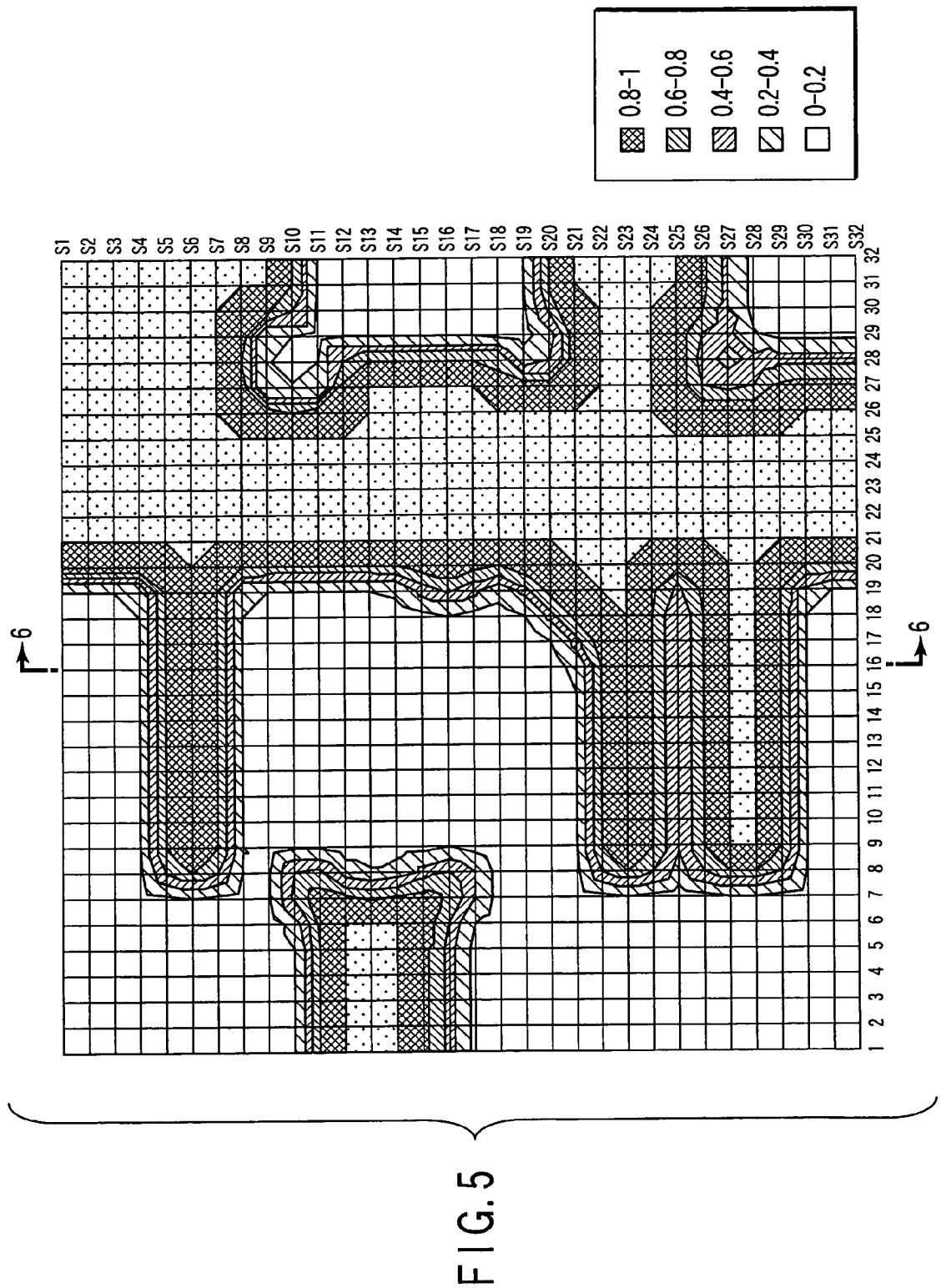
FIG. 5 is a graph showing data (processing data) obtained by carrying out calculation in accordance with a first processing step to the graphic data shown in FIG. 3.

By carrying out this calculation, the pattern data shown in FIG. 3 is transformed into pattern data (graphic data) shown in FIG. 5. FIG. 6 is a graph showing a profile of the graphic data shown in FIG. 5, taken along the lines 6-6 shown in FIG. 5.

This calculation is referred to as a so-called convoluting integration. By carrying out this calculation, a first processing data is obtained. By this calculation, corner portions of the rectangular graphic shape are rounded, and each graphic shape is smoothened. In addition, the profile is also smoothened. A numeral "4" in formula (1) is an example of a parameter as a first coefficient. This parameter is optimized so that the pattern data obtained through the calculation according to formula (1) becomes as close to sensed data as possible. Accordingly, this numeral changes depending on a mask pattern. In addition, a numeral "8" in formula (1) is defined by "4"×2, and thus when parameter "4" changes, this numeral changes accordingly.

Following the calculation of formula (1) above, a calculation (second processing step: step S2) shown below is carried out.

$$a(i,j)=\max[\{a(i,j)-0.1\}/0.9,0] \quad (2)$$

By carrying out this calculation, a second processing data is obtained. That is, by carrying out this calculation, the pattern data (graphic data) shown in FIG. 5 is transformed into a pattern data (graphic data) shown in FIG. 7. FIG. 8 is a graph showing a profile of the graphic data shown in FIG. 7, taken along the line 8-8 shown in FIG. 7. By carrying out this calculation, a position of a boundary (in particular, an inclination of the bottom portion of the profile) can be changed.

Here, with respect to max(Q, 0), 0 is selected when Q is equal to or smaller than 0. If Q exceeds 0, Q is selected. Therefore, formula (2) means that the gradation values of the pixels of the first processing data (i.e., pattern data shown in FIG. 5, obtained by carrying out calculation of formula (1)) is rounded up by a first threshold value "0", to provide the second processing data. In addition, a single parameter in Formula (2) is "0.1", and "0.9" is normalized by "1−0.1". As is the case with formula (1), this parameter is also optimized so that the pattern data obtained through the calculation according to formula (2) becomes as close to sensed data as possible. Accordingly, this numeral changes depending on a mask pattern.

Next, a following calculation (third processing step: step S3) is carried out to provide a third processed data.

$$a(i,j)=\min\{a(i,j)0.9,1\} \quad (3)$$

Figure 7:
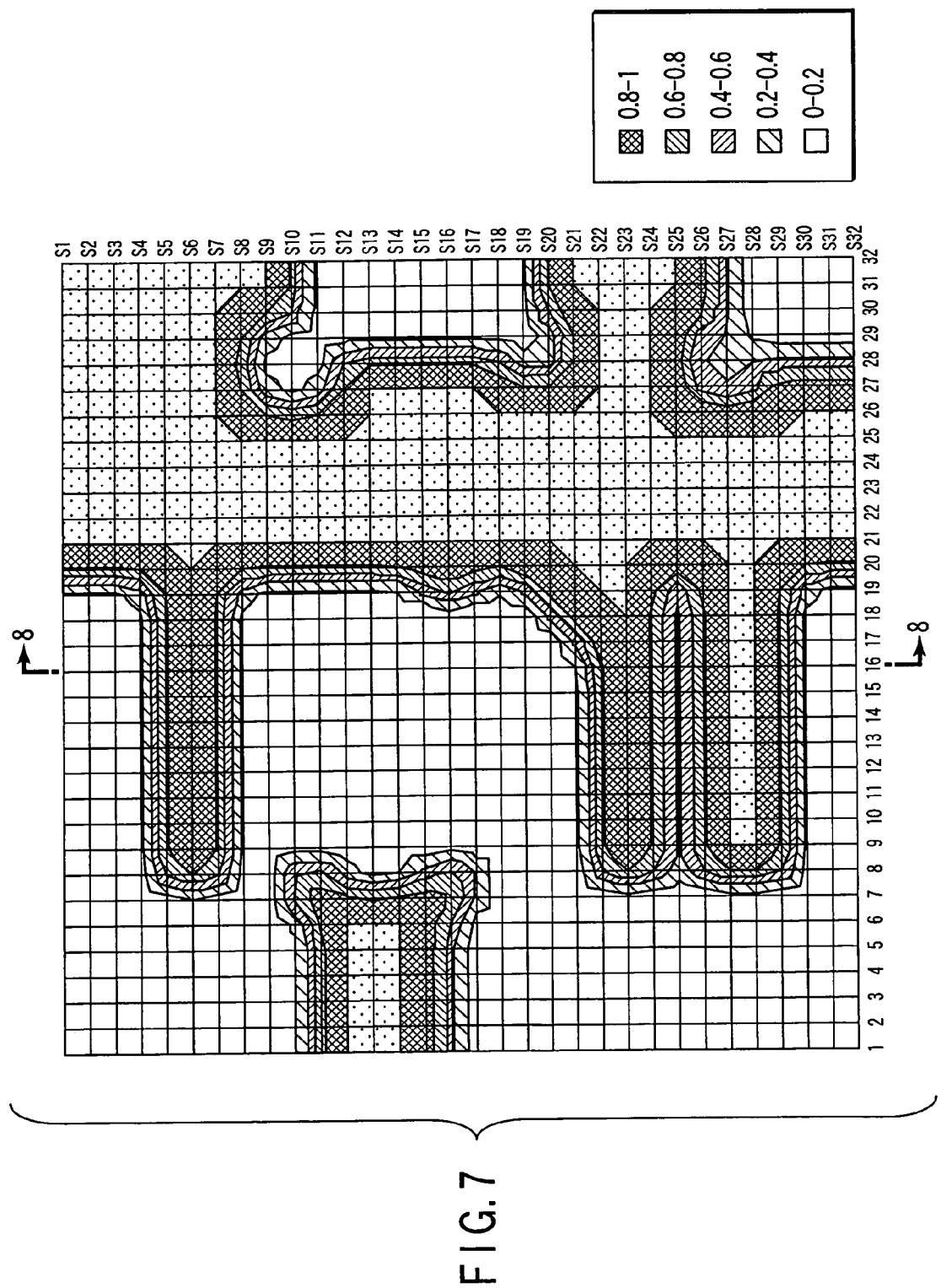
FIG. 7 is a graph showing data (processing data) obtained by carrying out calculation in accordance with a second processing step to the graphic data shown in FIG. 5.
Figure 8:
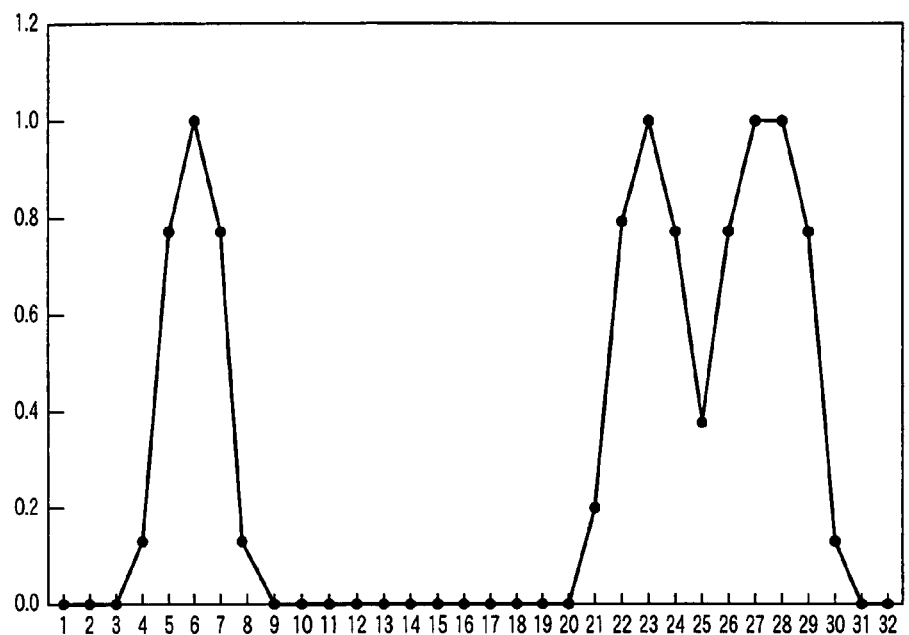
FIG. 8 is a graph showing a profile of the processing data shown in FIG. 7, taken along the line 8-8 shown in FIG. 7.
Figure 10:
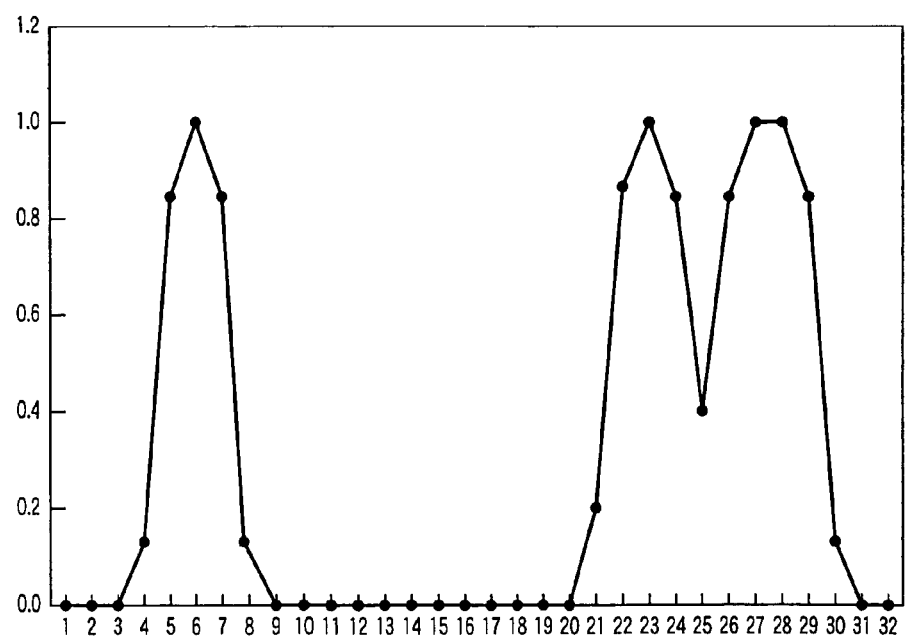
FIG. 10 is a graph showing a profile of the processing data shown in FIG. 9, taken along the line 10-10 shown in FIG. 9.
Figure 9:
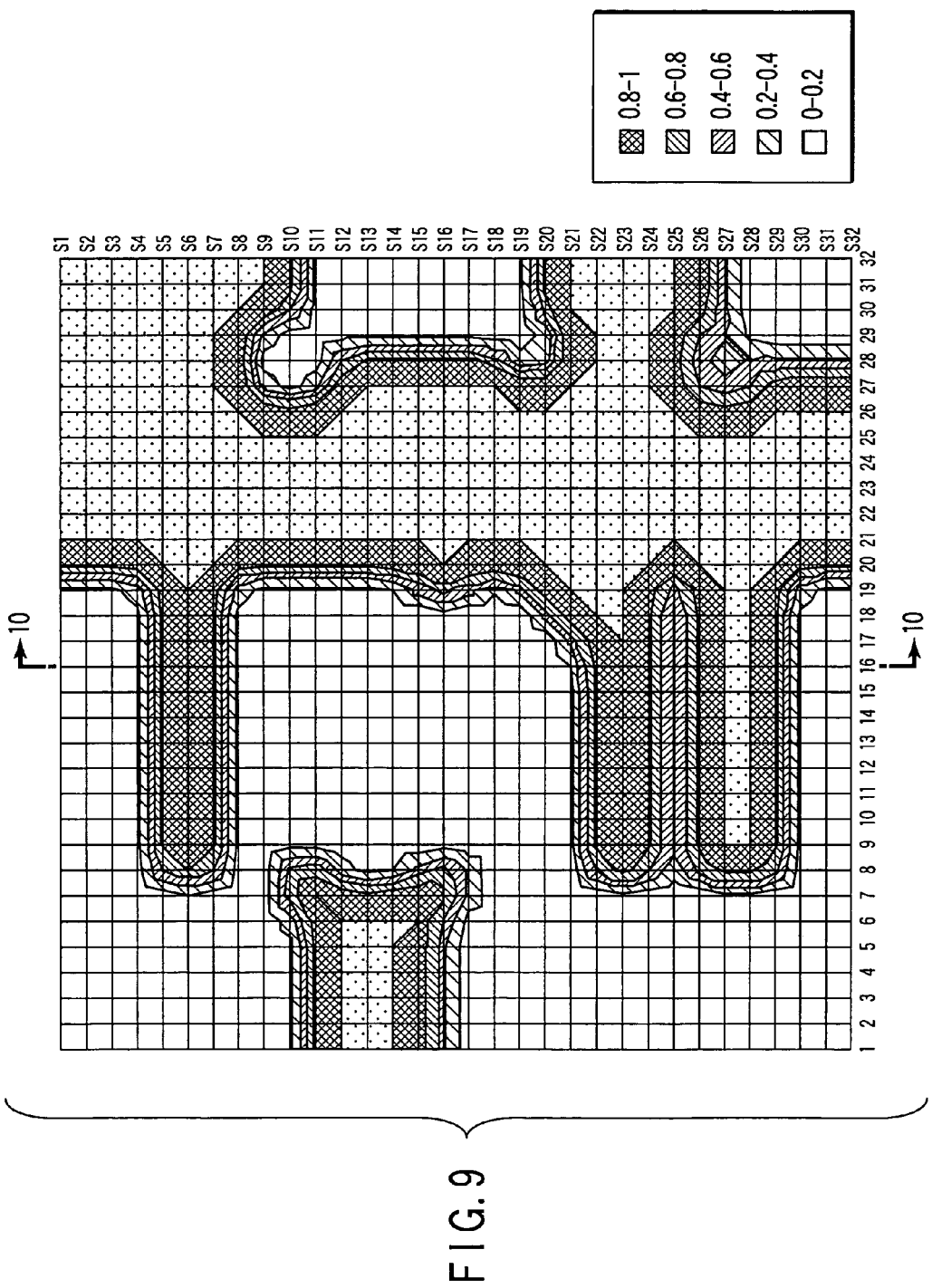
FIG. 9 is a graph showing data (processing data) obtained by carrying out calculation in accordance with a third processing step to the graphic data shown in FIG. 7.

By carrying out this calculation, the pattern data (graphic data) shown in FIG. 7 is transformed into a pattern data (graphic data) shown in FIG. 9. FIG. 10 is a graph showing a profile of the graphic data shown in FIG. 9, taken along the line 10-10 shown in FIG. 9. By carrying out this calculation, a profile and position of the pattern end (in particular, an inclination of the top portion of the profile) can be adjusted.

With respect to min(Q, 1), 1 is selected when Q is equal to or larger than 1. If Q is smaller than 1, Q is selected. Therefore, formula (3) means that the gradation values of the pixels in the second processing data (i.e., pattern data shown in FIG. 7, obtained by carrying out calculation of formula (1)) are rounded down by a second threshold value "1", to provide the third processing data. In addition, a single parameter in Formula (3) is "0.9". As is the case with formulae (1) and (2), this parameter is also optimized so that the pattern data obtained through the calculation according to formula (3) becomes as close as possible to sensed data. Accordingly, this numeral changes depending on a mask pattern.

Thereafter, a following calculation (fourth processing step: step S4) is carried out to provide a fourth processed data.

$$a(i,j)=a(i,j)^{1.2} \quad (4)$$

Formula (4) means that gradated values of the pixels in the third processed data are squared by a second coefficient "1.2" to generate the fourth processed data. By carrying out this calculation, the pattern data (graphic data) shown in FIG. 9 is transformed into a pattern data (graphic data) shown in FIG. 11. FIG. 12 is a graph showing a profile of the graphic data shown in FIG. 11, taken along the line 12-12 shown in FIG. 11. By carrying out this calculation, a profile of the pattern end (in particular, an inclination of the top and the bottom portion of the profile) can be changed.

The profile position and/or inclination is changed in the second, third and fourth steps. A major change (resize) is made in the second and third processing steps, and a minor change (fine adjustment) is made in the fourth processing step.

Next, a following calculation (fifth processing step: step S5) is carried out to provide a fifth processed data.

$$a(i,j)=[a(i,j)-\{1-a(i,j)\}\times 0.1^{1/2}]^2 \quad (5)$$

Figure 11:
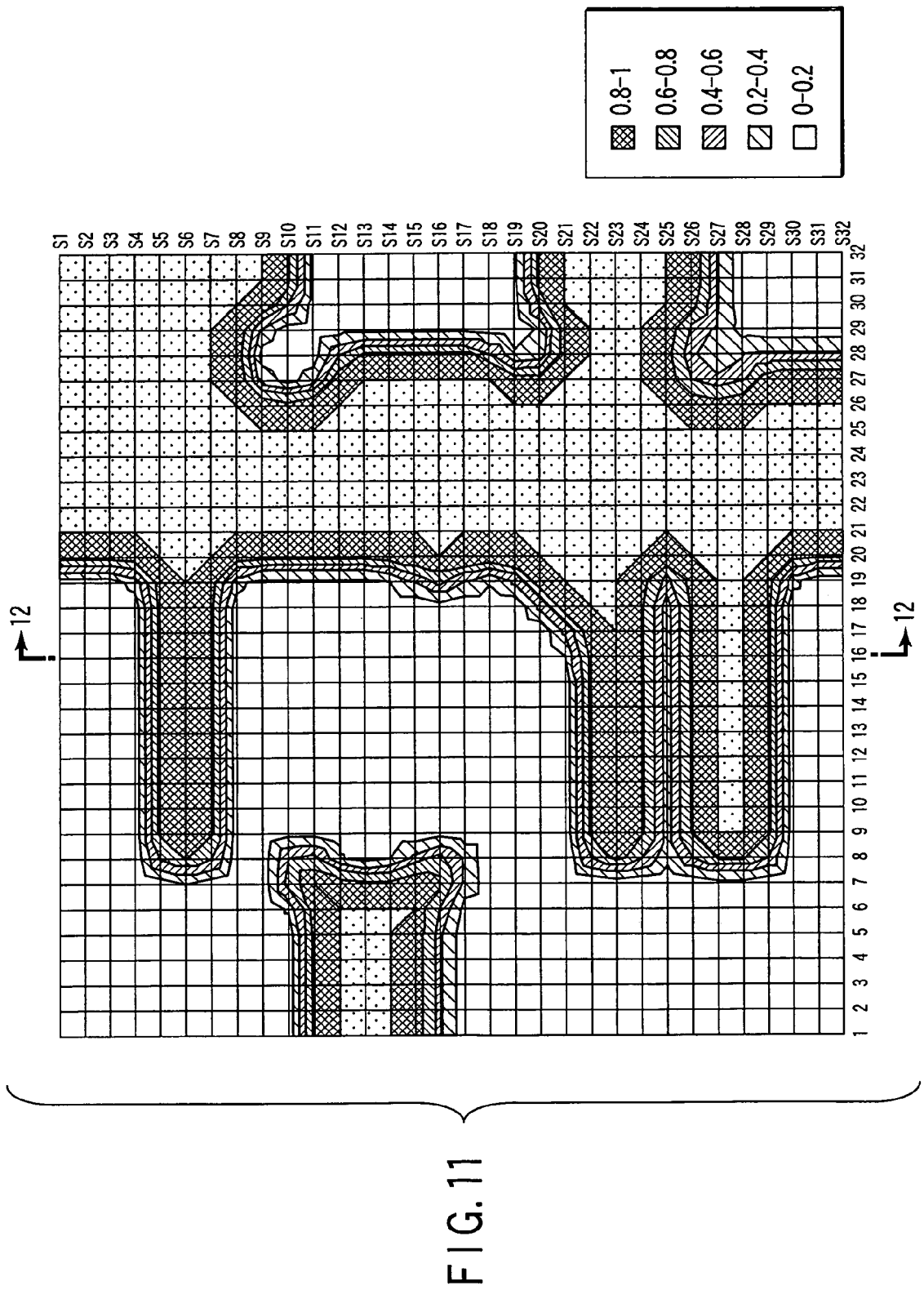
FIG. 11 is a graph showing data (processing data) obtained by carrying out calculation in accordance with a fourth processing step to the graphic data shown in FIG. 9.
Figure 13:
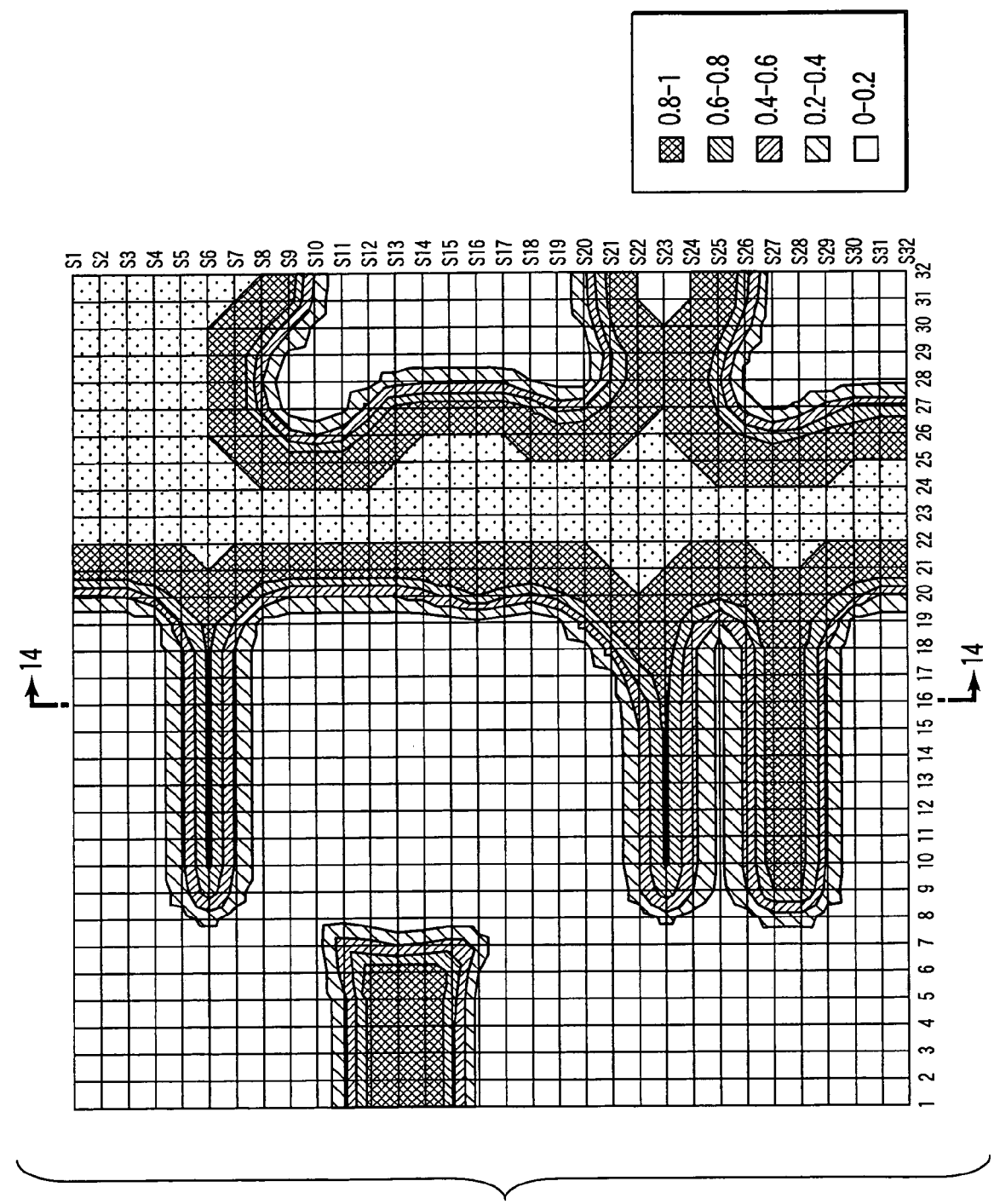
FIG. 13 is a graph showing data (processing data) obtained by carrying out calculation in a fifth processing step to the graphic data shown in FIG. 11.

By carrying out this calculation, the pattern data (graphic data) shown in FIG. 11 is transformed into a pattern data (graphic data) shown in FIG. 13. FIG. 14 is a graph showing a profile of the graphic data shown in FIG. 13, taken along the line 14-14 shown in FIG. 13.

Formula (5) means that gradated values obtained by calculating gradated values of the pixels in the fourth processed data by using a third coefficient "0.1" are squared to provide a fifth processed data.

By carrying out this calculation, it becomes possible to change a profile considering a phase effect in the case of using a half tone, for example.

After the step S4 (step S10), it is determined whether or not a phase effect is utilized. In the case of a general chrome mask that does not utilize the phase effect, this fifth processing step can be omitted.

Then, a following calculation (sixth processing step: step S6) is carried out to generate a sixth processed data.

$$a(i,j)=a(i,j)\times 210 \quad (6)$$

Figure 15:
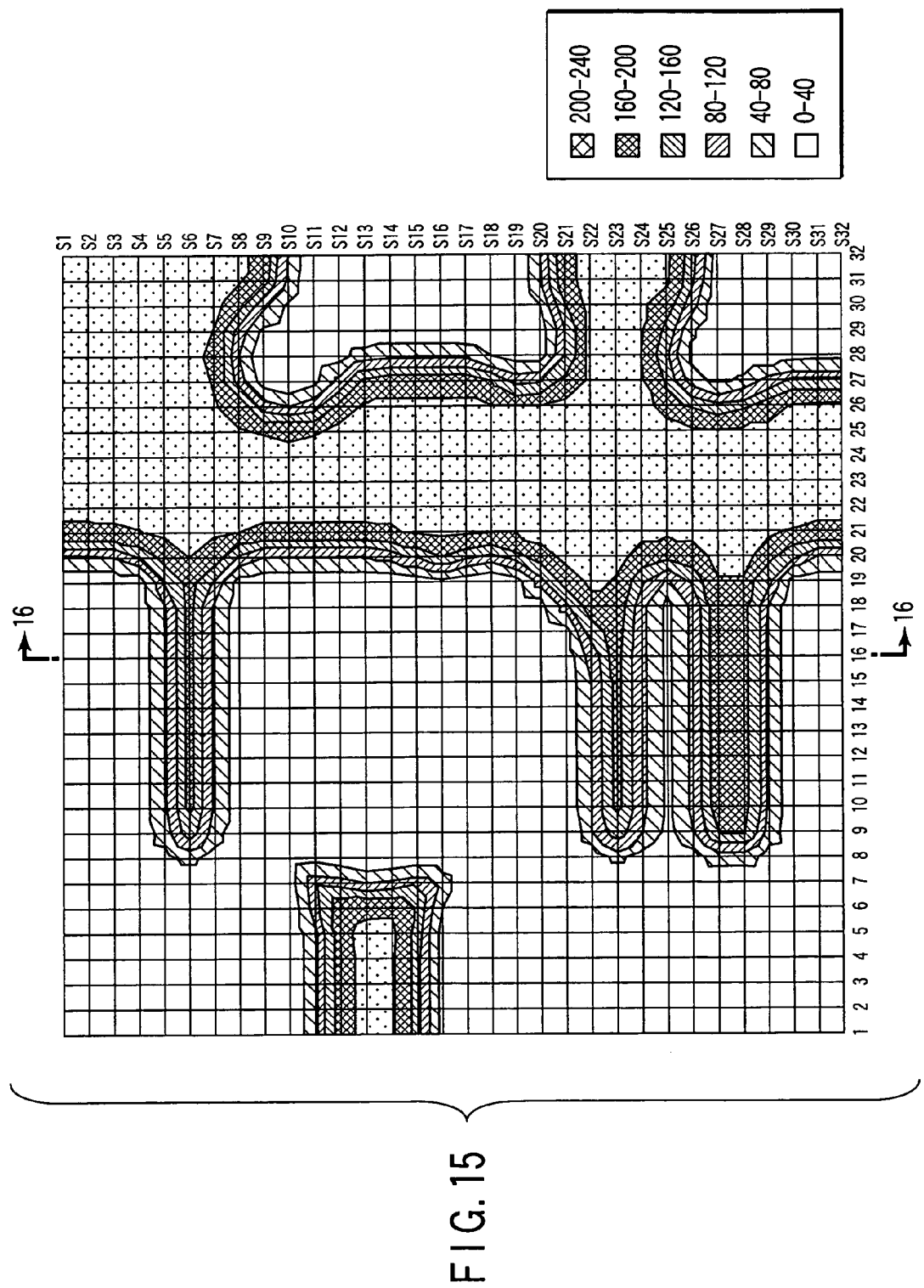
FIG. 15 is a graph showing data (processing data) obtained by carrying out calculation in accordance with a sixth processing step to the graphic data shown in FIG. 13.
Figure 16:
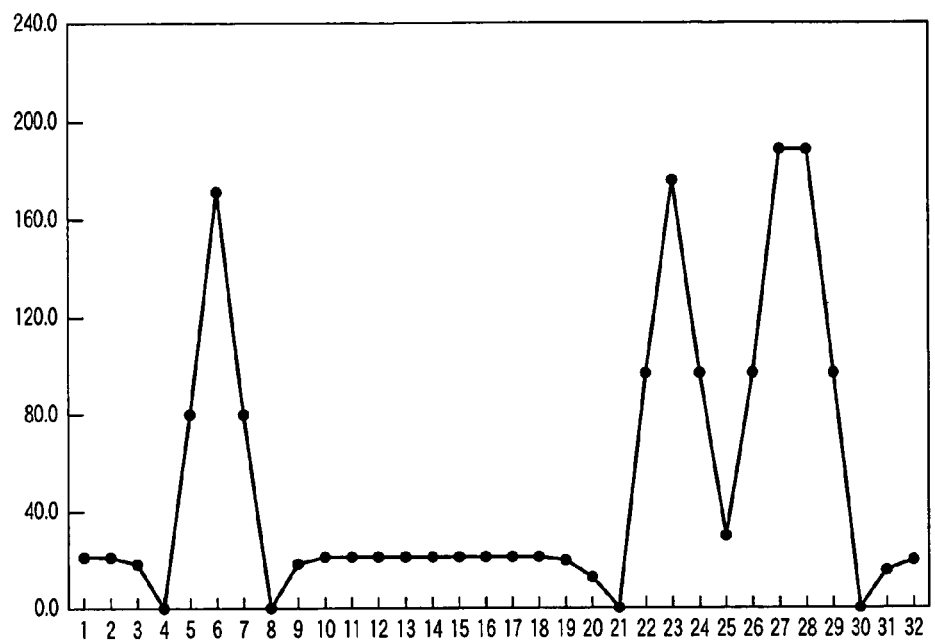
FIG. 16 is a graph showing a profile of the processing data shown in FIG. 15, taken along the line 16-16 shown in FIG. 15.

By carrying out this calculation, the pattern data (graphic data) shown in FIG. 13 is transformed into a pattern data (graphic data) shown in FIG. 15. FIG. 16 is a graph showing a profile of the graphic data shown in FIG. 15, taken along the line 16-16 shown in FIG. 15.

Formula (6) means that gradated values of the pixels in the fifth processed data are multiplied by a fourth coefficient "210" to generate a sixth processed data.

With the this calculation, a strength of the profile can be changed. That is, a dynamic range of the processed data can be set for the sensed data.

Subsequently, a following calculation (seventh processing step: step S7) is carried out to provide a seventh processed data.

$$a(i,j)=a(i,j)+10 \quad (7)$$

Figure 18:
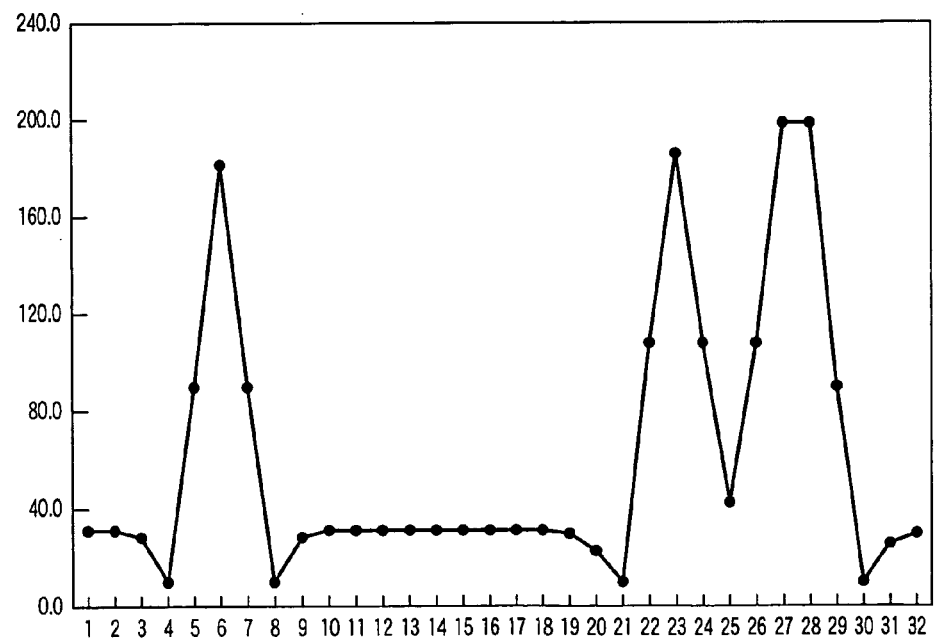
FIG. 18 is a graph showing a profile of the processing data shown in FIG. 17, taken along the line 18-18 shown in FIG. 17.
Figure 17:
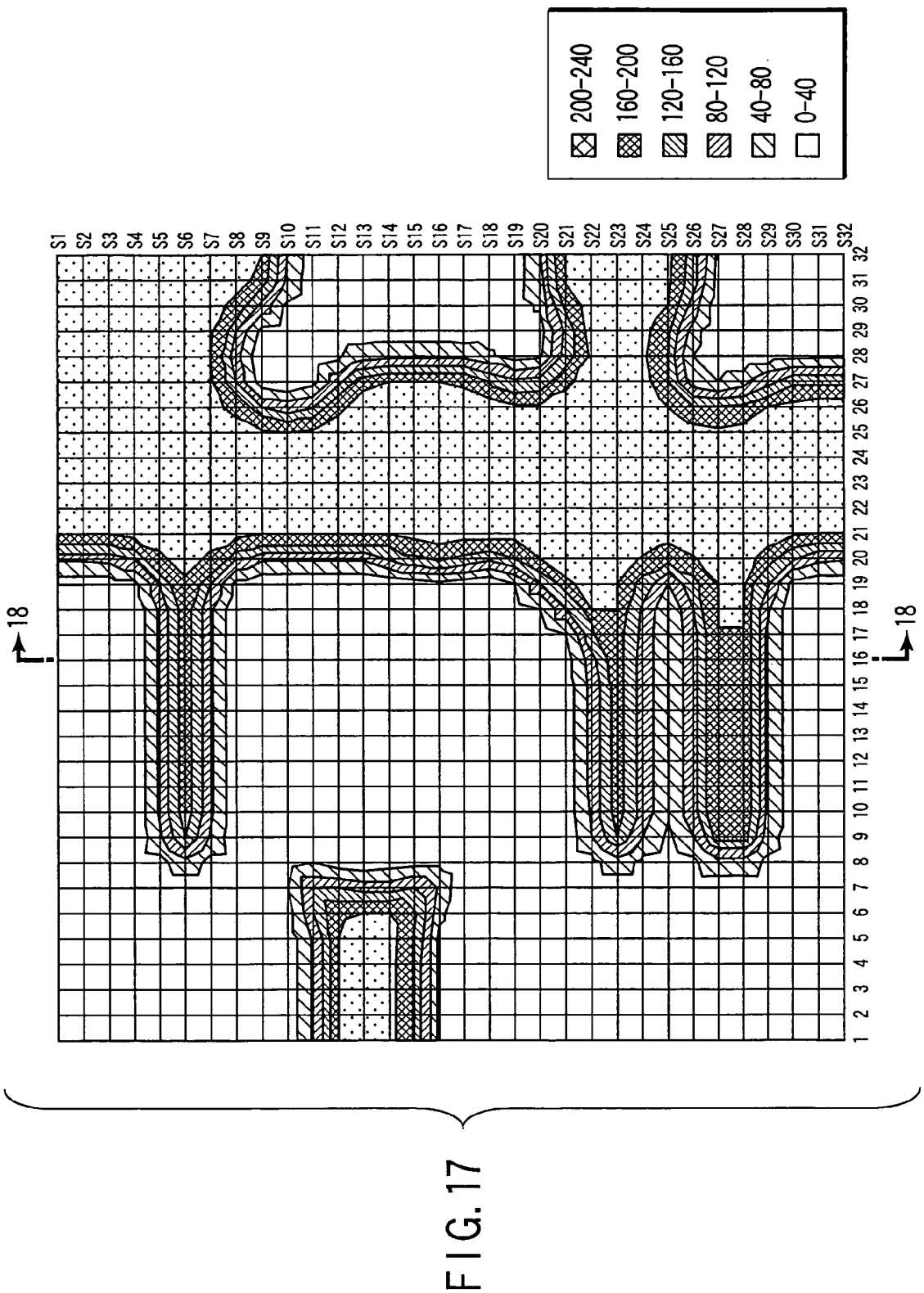
FIG. 17 is a graph showing data (processing data) obtained by carrying out calculation in accordance with a seventh processing step to the graphic data shown in FIG. 15.

By carrying out this calculation, the pattern data (graphic data) shown in FIG. 15 is transformed into a pattern data (graphic data) shown in FIG. 17. FIG. 18 is a graph showing a profile of the graphic data shown in FIG. 17, taken along the line 18-18 shown in FIG. 17.

Formula (7) means that gradated values of the pixels in the sixth processed data are added to a fifth coefficient "10" to generate the seventh processed data. By carrying out this calculation, a level of the base can be changed. That is, an offset for the processed data can be arbitrarily set.

By carrying out the above calculations from the step S1 to the step S7, the gradated data obtained from a design data of a pattern to be formed can be approximated to the sensed data.

Next, the obtained seventh processing data as shown in FIG. 17 is defined as a reference data, and the sensor data is compared with the reference data by the defect check circuit 18, to check pattern defect (step S20).

In the above calculations, as described above, a multi-stepped calculation scheme is used in order to obtain a reference data from a pattern design data and a single parameter is used for each calculation. In this manner, it becomes possible to make parameter adjustment independently for each calculation to calculate a parameter that can minimize a difference between the reference data and the sensed data. Thus, there is no limitation to optical radiation such as the wavelength or NA (Numerical Aperture) of a light beam source of a checking apparatus. Therefore, a time required for calculation can be reduced, and also it becomes possible to provide a reference data with high accuracy of alignment with a sensed data for a short period of time.

Accordingly, also in a phase shift mask or a mask using an ultra-high resolution technique such as optical proximity effect correction, a level difference between the sensed data and the reference data is eliminated, and a precious defect check can be attained.

Next, a method of manufacturing a MOS (Metal Oxide Semiconductor) transistor as an example of semiconductor devices, by using a mask having been pattern defect checked according to the pattern defect checking method as above-described, will be explained.

As shown in FIG. 19, a gate insulating film 32 is formed on a silicon semiconductor substrate 31 by using a thermal oxidation method, a polysilicon film 33 is formed on the gate insulating film 32 by CVD (Chemical Vapor Deposition) method. After that, the polysilicon film 33 and the gate insulating film 32 are subjected to patterning to form a gate structure comprised of the polysilicon film 33 and the gate insulating film 32. To form this gate structure, a photo resist layer 34 is formed on the polysilicon film 33, and then the photo resist layer 34 is patterning-processed by lithography to form a photo resist pattern.

At this patterning of the photo resist layer 34, use is made of a mask 35 having been pattern defect checked according to the pattern defect checking method as above-described. To be specific, the mask 35 is mounted above the silicon semiconductor substrate 31, and light beams are radiated onto the silicon semiconductor substrate 31 via the mask 35 from a light beam source, not shown, to transfer a pattern of the mask 35 to the photo resist layer 34. Subsequently, the photo resist layer 34 is patterning-processed by lithography so that a photo resist pattern 34 corresponding to the pattern of the mask 35 is formed, as shown in FIG. 20.

Next, as shown in FIG. 21, the polysilicon film 33 and the gate insulating film 32 are patterning-processed to form the gate structure comprised of the polysilicon film 33 and the gate insulating film 32, by using the photo resist pattern 34 as an etching mask. Then, impurities are implanted into the silicon semiconductor substrate 31 to form source/drain regions 36, by using the photo resist pattern 34, the polysilicon film 33 (polysilicon electrode) and the gate insulating film 32, as a mask.

Subsequently, the photo resist pattern 34 is removed by a known method. Then, as shown in FIG. 22, an interlayer insulating film 37 is formed over the silicon semiconductor substrate 31 by CVD method. Following this, openings are formed in the interlayer insulating film 37 for contact to the polysilicon electrode 33 and source/drain regions 36. To form the openings, a photo resist layer 38 is formed on the interlayer insulating film 37, and then the photo resist layer 38 is patterning-processed by lithography to form a photo resist pattern.

Figure 23:
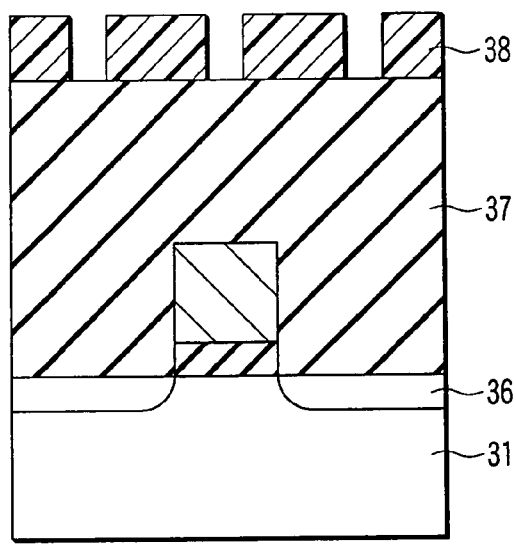
FIG. 23 is a cross sectional view showing a device structure in a step following to the step in FIG. 22 of the method of manufacturing the semiconductor device according to the embodiment of the present invention, which is used to explain the manufacturing method of the semiconductor device.

At this patterning of the photo resist layer 38, use is made of a mask 39 having been pattern defect checked according to the pattern defect checking method as above-described. To be specific, the mask 39 is mounted above the silicon semiconductor substrate 31, and light beams are radiated onto the silicon semiconductor substrate 31 via the mask 39 from a light beam source, not shown, to transfer a pattern of the mask 39 to the photo resist layer 38. Subsequently, the photo resist layer 38 is patterning-processed by lithography so that a photo resist pattern 38 corresponding to the pattern of the mask 39 is formed, as shown in FIG. 23.

Figure 24:
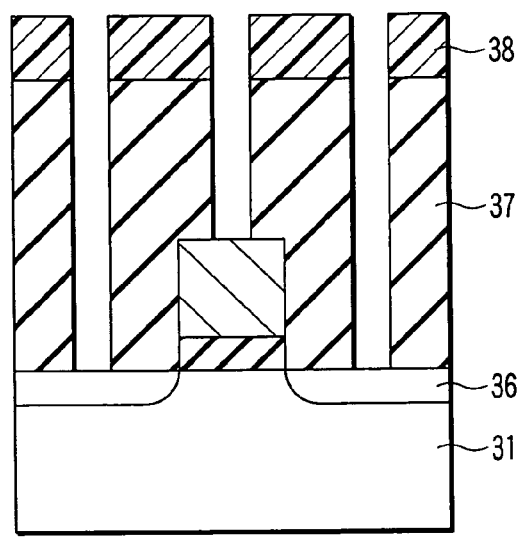
FIG. 24 is a cross sectional view showing a device structure in a step following to the step in FIG. 23 of the method of manufacturing the semiconductor device according to the embodiment of the present invention, which is used to explain the manufacturing method of the semiconductor device.

Next, as shown in FIG. 24, the interlayer insulating film 37 is patterning-processed to form the openings for contact to the polysilicon electrode 33 and source/drain regions 36, by using the photo resist pattern 38 as an etching mask.

Figure 25:
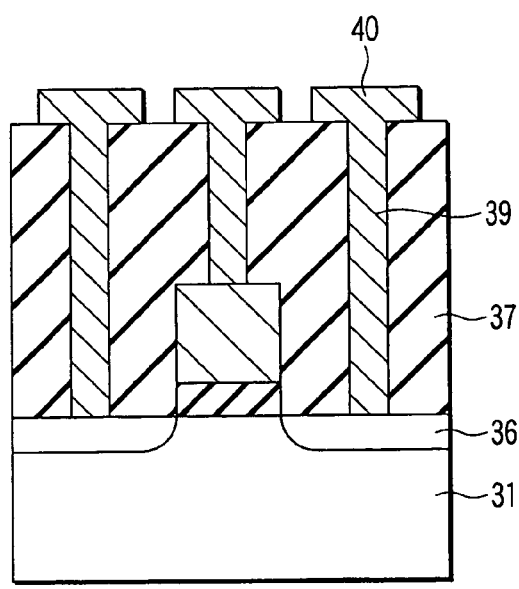
FIG. 25 is a cross sectional view showing a device structure in a step following to the step in FIG. 24 of the method of manufacturing the semiconductor device according to the embodiment of the present invention, which is used to explain the manufacturing method of the semiconductor device.

Subsequently, the photo resist pattern 38 is removed by a known method. Then, as shown in FIG. 25, contact metals 39 are formed in the openings for contact to the polysilicon electrode 33 and source/drain regions 36, and wiring metals 40 contacting the contact metals 39 are formed on the interlayer insulating film 37 by a known method. With the manufacturing method, since a mask 35 having been pattern defect checked according to the pattern defect checking method as above-described is used, the transferred mask pattern has high alignment with the reference data transferred, resulting in providing high accuracy to the semiconductor device thus formed.

The present invention is not limited to the above-described embodiments. In the embodiments, although the calculations of formula (1) to formula (6) have been carried out each one time. However, the calculation number, calculation sequence and the coefficients used for each calculation can be changed so that approximation between the reference data and the sensor data is enhanced. Further, the reference data may be obtained for each mask or may be obtained for each typical pattern.

In addition, in the case where the pattern defect checking method according to the embodiment is applied to a general chrome mask that does not utilize a phase effect, the fifth processing step can be omitted. Further, although the sixth and seventh processing steps are steps to adjust the reference data to an output level of the detecting circuit, these processing steps are not necessarily required when the detecting circuit can adjust the level of the sensed data to the reference data.

Moreover, the above calculation method can be written as a program which can be executed by a computer, for example, in a recording medium such as a magnetic disk (such as a floppy (registered trademark) disk and a hard disk), an optical disk (such as a CD-ROM and a DVD), or a semiconductor memory. Also, the calculation method can be transmitted by a communication medium. A computer carrying out the above embodiments may be a computer, which reads a program recorded in a recording medium, and executes the above-described processing in accordance with the program.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of generating reference data for use in a comparison with sensed data obtained by picking up an image of a pattern formed on an object, the method comprising:

generating, in a pattern expanding circuit, a two-value or multi-value gradated data of pixels in units of pixels from a design data, and generating first processed data by multiplying a gradated value of a pixel targeted in the gradated data by a first coefficient determined in accordance with gradated values of pixels located at a periphery of the targeted pixel; and generating, in a reference data generation circuit;

second processed data by rounding up a gradated value of the pixel in the first processed data by a first threshold value;

third processed data by rounding down a gradated value of the pixel in the second processed data by a second threshold value;

fourth processed data by raising a gradated value of the pixel in the third processed data to a power of a second coefficient; and reference data based on the fourth processed data.

2. A method of generating reference data, according to claim 1, wherein, in generating the first to fourth processed data, values of the coefficients in the first to fourth processed data are sought, that minimize a difference between the reference data and the sensed data, and the reference data is obtained by using the coefficients having the sought values.

3. A method of generating reference data, according to claim 1, wherein each of the first to fourth processed data contains one coefficient as the coefficient, and the coefficients of the first to fourth processed data are independently changeable.

4. A method of generating reference data, according to claim 2, wherein each of the first to fourth processed data contains one coefficient as the coefficient, and the coefficients of the first to fourth processed data are independently changeable.

5. A pattern defect detecting apparatus in which sensed data obtained by picking up an image of a pattern formed on an object is compared with reference data obtained by developing design data of the pattern to detect a defect of the pattern, the apparatus comprising:

a generating circuit configured to generate a two-value or multi-value gradated data of pixels in units of pixels from the design data, and to generate first processed data by multiplying a gradated value of a pixel targeted in the gradated data by a first coefficient determined in accordance with gradated values of pixels located at a periphery of the targeted pixel;

a generating circuit configured to generate second processed data by rounding up a gradated value of the pixel in the first processed data by a first threshold value;

a generating circuit configured to generate third processed data by rounding down a gradated value of the pixel in the second processed data by a second threshold value;

a generating circuit configured to generate fourth processed data by raising a gradated value of the pixel in the third processed data to a power of a second coefficient;

a generating circuit configured to generate reference data based on the fourth processed data; and a defect detecting circuit configured to detect a defect of the pattern by comparing the reference data with the sensed data.

6. A computer-readable medium storing a reference data generating program readable and executable by a computer, to perform a method in which reference data for use in a comparison with sensed data obtained by picking up an image of a pattern formed on an object is generated, the method comprising:

generating a two-value or multi-value gradated data of pixels in units of pixels from a design data, and generating first processed data by multiplying a gradated value of a pixel targeted in the gradated data by a first coefficient determined in accordance with gradated values of pixels located at a periphery of the targeted pixel;

generating second processed data by rounding up to a gradated value of the pixel in the first processed data by a first threshold value;

generating third processed data by rounding down a gradated value of the pixel in the second processed data by a second threshold value;

generating fourth processed data by raising a gradated value of the pixel in the third processed data to a power of a second coefficient; and generating reference data based on the fourth processed data.

7. A pattern defect detecting apparatus in which sensed data obtained by picking up an image of a pattern formed on an object is compared with reference data obtained by developing design data of a pattern to be formed on the object to detect a defect of the pattern formed on the object, the apparatus comprising:

a gradated data generating circuit configured to generate a two-value or multi-value gradated data of pixels in units of pixels from the design data;

a reference data generating circuit configured to generate a first processed data by multiplying a gradated value of a pixel targeted in the gradated data by a first coefficient determined in accordance with gradated values of pixels located at a periphery of the targeted pixel, second processed data by rounding up a gradated value of the pixel in the first processed data by a first threshold value, third processed data by rounding down a gradated value of the pixel in the second processed data by a second threshold value, fourth processed data by raising a gradated value of the pixel in the third processed data to a power of a second coefficient, and reference data based on the fourth processed data; and a defect detecting circuit configured to detect a detect of the pattern by comparing the reference data with the sensed data, in which the pattern to be formed on the object is a phase shift pattern, and the reference data generating circuit is configured to further generate fifth processed data by squaring a gradated value obtained by multiplying a gradated value of the pixel in the fourth processed data by a third coefficient, the fifth processed data being used as the reference data.

8. A pattern defect detecting apparatus according to claim 7, in which the reference data generating circuit is configured to further generate a sixth processed data by multiplying a gradated value of the pixel in the fourth or fifth processed data by a fourth coefficient, a seventh processed data by adding a gradated value of the pixel in the sixth processed data to a fifth coefficient, the seventh processed data being used as the reference data.

9. A method of detecting a pattern defect, in which a sensed data obtained by picking up an image of a pattern formed on an object is compared with reference data obtained by developing design data of the pattern formed on the object to detect a defect of the pattern formed on the object, comprising:

generating, in a pattern expanding circuit, two-value or multi-value gradated data of pixels in units of pixels from the design data, and generating first processed data by multiplying a gradated value of a pixel targeted in the gradated data by a first coefficient determined in accordance with gradated values of pixels located at the periphery of the targeted pixel;

generating, in a reference data generation circuit:

second processed data by rounding up a gradated value of the pixel in the first processed data by a first threshold value;

third processed data by rounding down a gradated value of the pixel in the second processed data by a second threshold value;

fourth processed data by raising a gradated value of the pixel in the third processed data to a power of a second coefficient; and reference data based on the fourth processed data; and detecting, in a defect check circuit, a defect of the pattern by comparing the reference data with the sensed data.

10. A method of manufacturing a semiconductor device comprising:

detecting a pattern defect of a photo mask having a semiconductor circuit pattern, by using a method of detecting a pattern defect, in which sensed data obtained by picking up an image of a pattern formed on an object is compared with reference data obtained by developing design data of the pattern formed on the object to detect a defect of the pattern formed on the object, the method comprising:

generating a two-value or multi-value gradated data of pixels in units of pixels from a design data, and generating first processed data by multiplying a gradated value of a pixel targeted in the gradated data by a first coefficient determined in accordance with gradated values of pixels located at a periphery of the targeted pixel;

generating second processed data by rounding up a gradated value of the pixel in the first processed data by a first threshold value;

generating third processed data by rounding down a gradated value of the pixel in the second processed data by a second threshold value;

generating fourth processed data by raising a gradated value of the pixel in the third processed data to a power of a second coefficient;

generating reference data based on the fourth processed data;

detecting a defect of the pattern by comparing the reference data with the sensed data;

transferring the semiconductor circuit pattern on a semiconductor substrate, by using the photo mask after detecting the pattern defect; and forming a semiconductor circuit having the semiconductor circuit pattern on the semiconductor substrate.

11. A pattern defect detecting apparatus, according to claim 5, wherein, in generating the first to fourth processed data, values of the coefficients in the first to fourth processed data are sought, that minimize a difference between the reference data and the sensed data, and the reference data is obtained by using the coefficients having the sought values.

12. A pattern defect detecting apparatus according to claim 5, wherein each of the first to fourth processed data contains one coefficient as the coefficient, and the coefficients of the first to fourth processed data are independently changeable.

* * * * *

UNITED STATES PATENT AND TRADEMARK OFFICE
CERTIFICATE OF CORRECTION

| | |
|---|---|
| PATENT NO. | : 7,602,961 B2 |
| APPLICATION NO. | : 11/024198 |
| DATED | : October 13, 2009 |
| INVENTOR(S) | : Yoshikawa et al. |

It is certified that error appears in the above-identified patent and that said Letters Patent is hereby corrected as shown below:

Claim 7, column 12, line 20, change "detect" to --defect--.

Signed and Sealed this

Eighth Day of December, 2009

David J. Kappos
*Director of the United States Patent and Trademark Office*